United States Patent [19]
Elliott

[11] Patent Number: 6,165,125
[45] Date of Patent: Dec. 26, 2000

[54] OTOSCOPE RETROFIT TO ALLOW MULTIPURPOSE USE

[76] Inventor: Peter Christopher Elliott, No. 2, Lakeside, Austin, Tex. 78746

[21] Appl. No.: 09/398,287

[22] Filed: Sep. 20, 1999

Related U.S. Application Data

[63] Continuation-in-part of application No. 09/306,210, May 6, 1999, Pat. No. 6,001,059.

[51] Int. Cl.[7] .................................................. A61B 1/227
[52] U.S. Cl. ........................................... 600/200; 600/184
[58] Field of Search .................................. 600/200, 199, 600/184

[56] References Cited

U.S. PATENT DOCUMENTS

| | | | |
|---|---|---|---|
| 1,624,716 | 4/1927 | Cerbo | 600/184 |
| 2,290,665 | 7/1942 | Armsen | 600/200 |
| 2,678,645 | 5/1954 | Raimo | 600/200 |
| 3,146,775 | 9/1964 | Moore et al. | 600/200 |
| 3,934,578 | 1/1976 | Heine | 600/200 |
| 4,380,998 | 4/1983 | Kieffer, III et al. | 600/200 |
| 4,785,796 | 11/1988 | Mattson | 600/200 |
| 5,873,819 | 2/1999 | Koch | 600/200 |
| 5,916,150 | 6/1999 | Sillman | 600/184 |
| 5,938,590 | 8/1999 | Elliott | 600/200 |
| 6,001,059 | 12/1999 | Elliott | 600/200 |

*Primary Examiner*—Paul J. Hirsch
*Attorney, Agent, or Firm*—Joseph F. Lung

[57] ABSTRACT

Mechanically operable extensions for an otoscope speculum holder to allow line of sight through the otoscope to manually position finger like projections around or over an object such as a bug or peanut and with finger pressure on a lever hold such object for manual removal by removing the otoscope.

5 Claims, 3 Drawing Sheets

OTOSCOPE RETROFIT TO ALLOW MULTIPURPOSE USE

This is a continuation-in-part of Ser. No. 09/306,210, filed May 6, 1999, now U.S. Pat. No. 6,001,059 inventor P. C. Elliott entitled "An otoscope retrofit to allow multipurpose use".

BACKGROUND

An otoscope is an instrument normally designed to allow a physician to peer inside an ear or into a nose through a lighted pathway. At times, particularly in infants, there are foreign bodies such as a bead or a bug within an ear or nose that necessitate removal. The objectives of this invention include low cost retrofitting of an otoscope to allow removal of foreign material including a bug from a nose and ear in a rapid patient comfortable manner.

The invention outlined in Ser. No. 09/306,210, now U.S. Pat. No. 6,001,059 includes about one eighth inch diameter flexible plastic tubing with a first end connectable to a controllable vacuum source and a second end leading to and connectable to a sidearm on the speculum in one embodiment and connectable to a sidearm on speculum extensions or retrofits in other embodiments. An insufflation port on the head of the otoscope may be partially or totally closed using finger pressure to engage or disengage the vacuum source. Normally with no external vacuum source the physician uses a small air bulb and finger pressure to vibrate the tympanic membrane in the inner ear to determine if there is fluid behind the tympanic membrane. In the invention size of the insufflation port and control of the vacuum source are such that with the insufflation port totally open there is essentially no vacuum in the otoscope. This continuation-in-part invention includes embodiments of the retrofitting units for attachment to the speculum receptacle or holder of the otoscope wherein the user without use of vacuum may manually pull a lever to partially close the ends of the retrofit units to hold a foreign body such as a bug in the tip of the retrofit unit for removal.

Minor changes to the speculum or the speculum retrofit units of the otoscope would be easily made but would be within the purview of the invention. We wish to be limited only to the spirit and purpose as outlined in these specifications and claims.

SUMMARY OF THE INVENTION

The invention encompasses simple low cost removable additions or retrofit units to allow a user to manually pull a lever to constrict finger like projections on the end of an otoscope retrofit unit and without interfering with the users line of sight to grapple or enclose a foreign body in the interior of an ear or a nose.

DETAILED DESCRIPTION OF THE INVENTION

The invention may best be described from the drawings.

Figure 1:
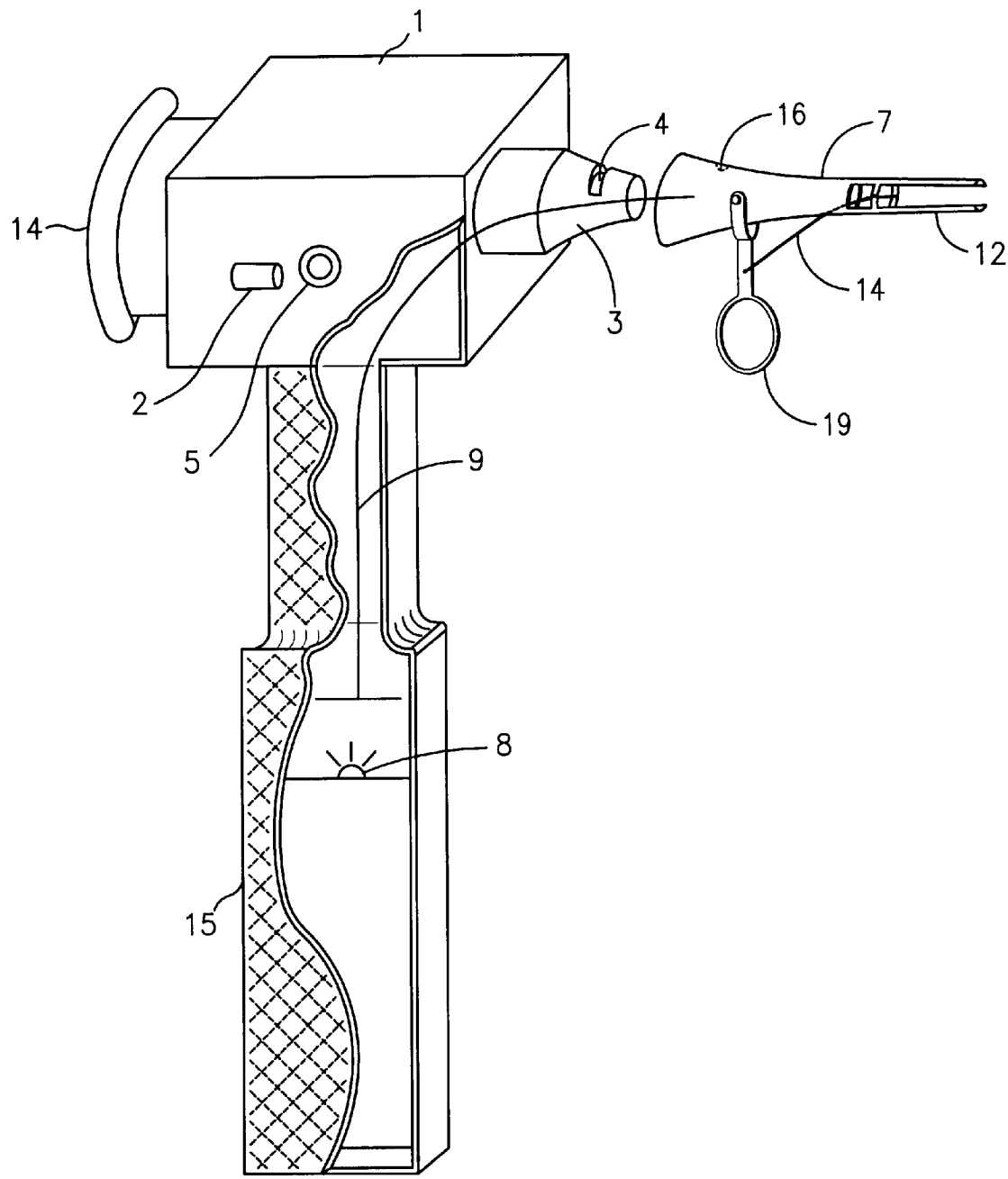
FIG. 1 shows an otoscope with a first embodiment of the retrofit unit that is an extension of the speculum in place.

In FIG. 1 an otoscope 1 head with an insufflation port 5 and handle 15 is shown. An electrically powered light 8 with a fiber optic bundle 9 furnishes light to the distal end of the cone shaped speculum receptacle or holder 3 through the retrofit extension 7 so that a viewer can see an interior of an ear or nose by looking through lens 14. The retrofit extension 7 may be twistably connected with the speculum holder 3 with ridge 16 twisting into slot 4.

Figure 2:
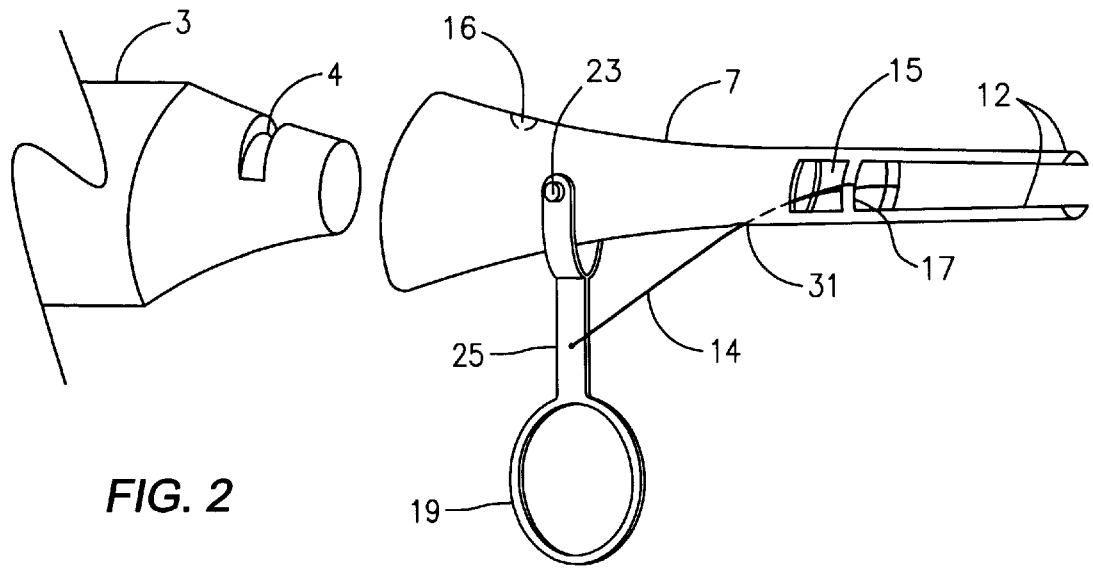
FIG. 2 shows a detail view of the first embodiment.

In FIG. 2 shows a larger view of the retrofit extension 7 with numbering the same as in FIG. 1. All embodiments of the three retrofit extensions are preferably made of a semi-rigid plastic and may have thinned portions to facilitate bending. In FIG. 2 dual fmger like extensions 12 are pulled together when fmger pressure against pull ring 19 moves lever 25 to pull string 14 attaching to each side of the thin plastic ring 17 and then passing through opening 31 to firmly attach to lever 25. Finger pressure in finger hole 19 depresses each side of plastic ring 17 to cause the fmger like projections 12 to move toward each other to trap or hold an object. The pull string 14 goes through opening 31 in back of the larger opening 15 that forms the thin plastic ring 17 that has string 14 attached on each side. Lever 25 is attached to unit 7 by snapping over posts 23 on each side of unit 7.

Figure 3:
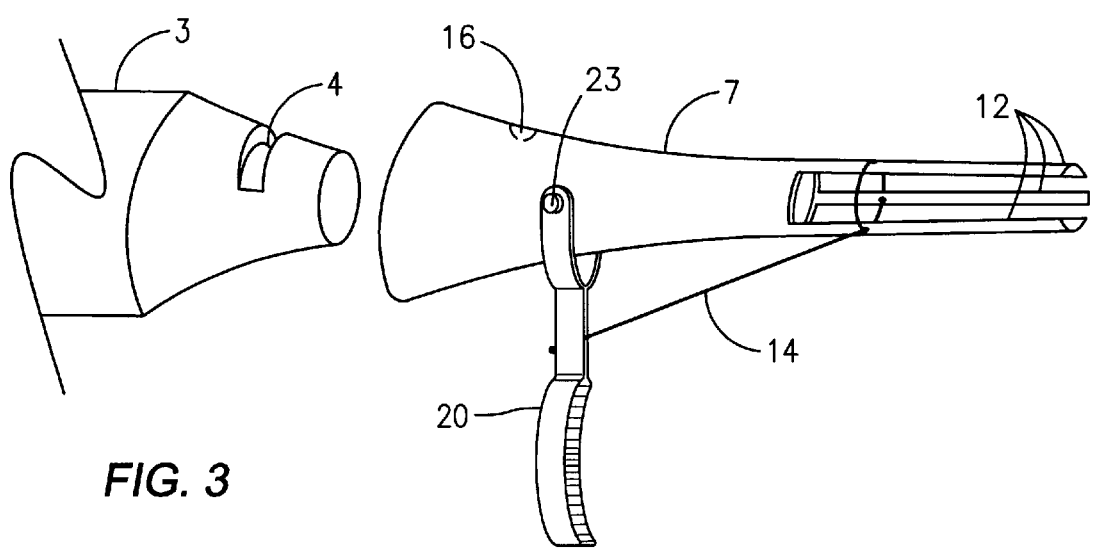
FIG. 3 shows a second embodiment wherein three finger-like projections are pulled to-gether to hold an object such as a bug.

FIG. 3 shows a second embodiment of the invention wherein pull string 14 which is attached to lever 18 is threaded through three finger-like projections 12 to pull these fingers toward each other to hold an object such as a bug when finger pressure is used to pull straight lever 18 toward the otoscope handle 15, FIG. 1.

Figure 4:
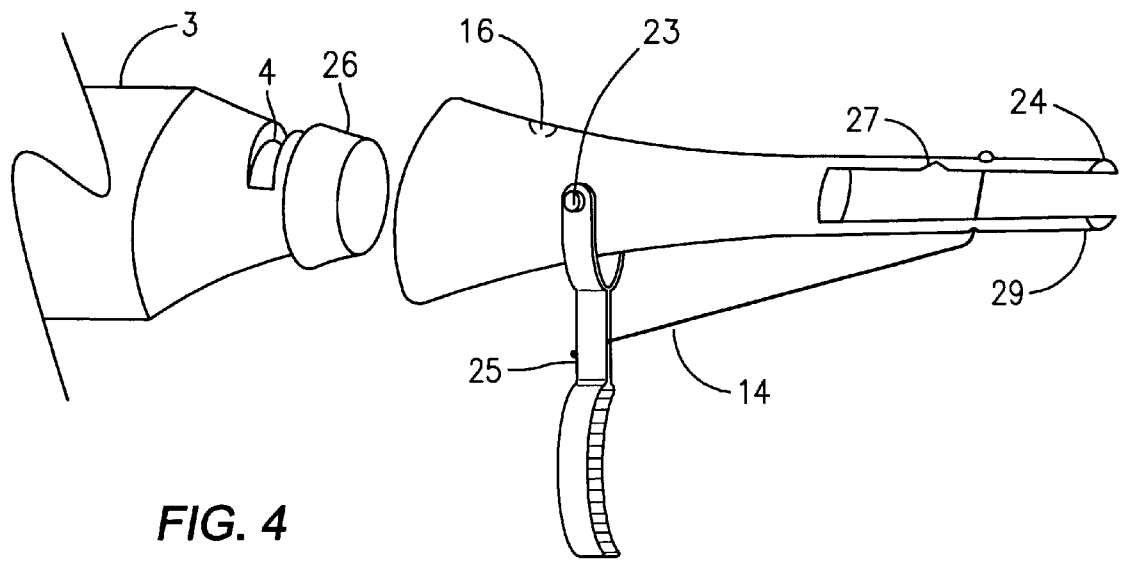
FIG. 4 shows a third embodiment wherein a hinged segment of a speculum extension is pulled against a stationary opposite segment to grab and hold an object for removal.
Figure 5:
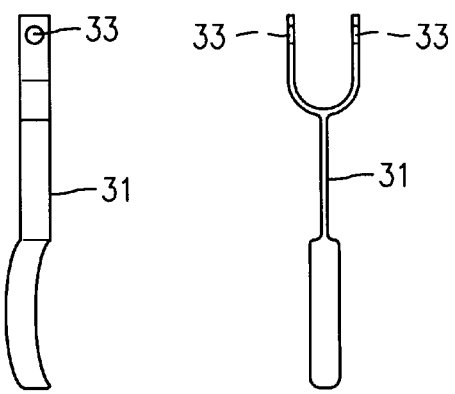
FIG. 5 shows a Y shaped lever that snaps over the speculum extensions in FIG. 2, FIG. 3, and FIG. 4 onto projections for hinging the lever.

FIG. 4 shows an embodiment with a clear bottom cuplike unit 26 covering the end of the speculum receptacle 3. The cuplike unit 26 may be also be used with retrofit embodiments shown in both FIG. 2 and FIG. 3.

In all embodiments the speculum and any connectors may be fabricated from any of several semi-rigid plastics or rubber with a heat sterilizable plastic being preferred. FIG. 4 has two finger like projections 24 and 29, preferably with projection 24 being narrower than projection 29 with projection 24 having a narrowed portion 27 to act as a hinge with pressure on lever 18 pulling string 14 to pull projection 24 against stationary projection 29 to hold an object. Other numbers on the drawing are as previously discussed. There is an essentially clear line of sight for the otoscope user in all embodiments.

What is claimed is:

1. Attachments for multipurpose use of an otoscope comprising:

a) an extension for a speculum on said otoscope, b) a projection to allow twistably fastening said extension to a speculum holder of said otoscope.

c) dual pins and a Y shaped lever with openings in each arm of said Y shaped lever to allow fastening said lever to said extension by snapping said arms over said pins, d) a pull string and finger like projection means on a beginning end of said extension;

said pull string connecting with said lever and with said finger like projection means to cause said finger like projection means to move toward each other to grapple and hold an object with finger pressure activation of said lever.

2. Attachments for multipurpose use of an otoscope as in claim 1 wherein said finger like projection means are finger like projections fastened on bottom end to a circular plastic ring with said pull string attached on each side of said circular plastic ring and acting to deform said ring to pull ends of said finger like projections together with finger pressure activation of said lever.

3. Attachments for a multipurpose use of an otosscope as in claim 1 wherein said finger like projection means comprise three finger fingerlike projections with a first end of said pull string attached about midway to one of said projections and is threaded through holes in both of the other of said projections and is fixably attached to said lever with activation of said lever pulling tip ends of said projections together.

4. Attachments for multipurpose use of an otoscope as in claim 1 comprising two finger like projections with a first one of said projections having a thinned area to act as a hinge with said pull string fixably attached toward a distal end of said first one of said projections and extending through a hole in a second one of said projections and extending through an opening in said retrofit unit to fixably attach to said lever to allow finger pressure on said lever to pull distal ends of said projections together.

5. Attachments for multipurpose use of an otoscope as in claim 1 further comprising a cuplike plastic unit with a clear bottom fittable over a distal end of said speculum holder, allowing line of sight to an object to be removed and acting to prevent a removed object from entering said otoscope head.

* * * * *